US007769435B2

(12) United States Patent
Kuo et al.

(10) Patent No.: US 7,769,435 B2
(45) Date of Patent: Aug. 3, 2010

(54) EARPHONE SENSOR SYSTEM FOR MEASURING ELECTROCARDIOGRAM SIGNALS

(75) Inventors: Terry B. J. Kuo, 7-F-2, No. 52, Beichang 5th St., Ji-An Township, Hualien County 973 (TW); Cheryl C. H. Yang, 7-F-2, No. 52, Beichang 5th St., Ji-An Township, Hualien County 973 (TW)

(73) Assignees: Terry B. J. Kuo, Ji-An Township, Hualien County (TW); Cheryl C. H. Yang, Ji-An Township, Hualien County (TW); Enjoy Research Inc., Ji-An Township, Hualien County (TW)

( * ) Notice: Subject to any disclaimer, the term of this patent is extended or adjusted under 35 U.S.C. 154(b) by 480 days.

(21) Appl. No.: 11/737,016

(22) Filed: Apr. 18, 2007

(65) Prior Publication Data
US 2008/0027340 A1    Jan. 31, 2008

(30) Foreign Application Priority Data
Jun. 21, 2006    (TW) .............................. 95122240 A

(51) Int. Cl.
*A61B 5/04*    (2006.01)
(52) U.S. Cl. .................... 600/509; 600/519; 600/523
(58) Field of Classification Search ................ 600/509, 600/523, 528; 327/561
See application file for complete search history.

(56) References Cited

U.S. PATENT DOCUMENTS

| 5,314,389 A | * | 5/1994 | Dotan ............................ 482/3 |
| 5,957,854 A | * | 9/1999 | Besson et al. ................ 600/509 |
| 7,065,396 B2 | * | 6/2006 | Hampton ..................... 600/509 |

OTHER PUBLICATIONS

MacArthur, John D. and Catherine. "Heart Rate Variability." Research Network on Socioeconomic Status and Health. Jun. 2, 2000. University of California, San Francisco. Jun. 20, 2009 <http://www.macses.ucsf.edu/Research/Allostatic/notebook/heartrate.html>.*

* cited by examiner

*Primary Examiner*—Mark W Bockelman
*Assistant Examiner*—Elizabeth K So
(74) *Attorney, Agent, or Firm*—Egbert Law Offices PLLC

(57) ABSTRACT

An earphone sensor system for measuring electrocardiogram signals provides convenient and comfortable noninvasive electrocardiogram signal measuring for a subject. The electrocardiogram signal measuring system includes an electrocardiogram signal analyzing apparatus and an earphone sensing apparatus. The electrocardiogram signal analyzing apparatus includes an amplifier module, a microcontroller, a display, a radio module and a housing having conductive contacts. The earphone sensing apparatus includes an earphone and an electrode. The electrode is disposed in the earphone, and can be electrically connected to the subject for collecting the weak electrocardiogram signal at the head of the subject. By contacting the body surface of the testee with the housing having conductive contacts and the electrode, a basic loop for collecting the electrocardiogram signals is formed. The earphone sensor system can be associated with commercial gadgets and used for musical treatments and bio-feedback.

15 Claims, 3 Drawing Sheets

EARPHONE SENSOR SYSTEM FOR MEASURING ELECTROCARDIOGRAM SIGNALS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to an electrocardiogram signal measuring system. More particularly, the present invention relates to an earphone sensor system for measuring electrocardiogram signals.

2. Description of Related Art Including Information Disclosed Under 37 CFR 1.97 and 37 CFR 1.98

Nowadays, as invasive measuring technology continues to develop, an alternative direction, i.e., noninvasive measuring technology, increasingly emerges. Compared with invasive measuring technology which often causes the subject to suffer, the noninvasive measuring technology uses tools and techniques without pain or injury to diagnose the function of the body viscera.

Because noninvasive measuring technology previously could not obtain exact electrocardiogram signals, the practicability thereof was not high. However, in recent years, signal detecting and processing techniques have been greatly improved, particularly in software engineering. The powerful operation capability of the computer can compensate for weaknesses of noninvasive measuring technology, so as to obtain valuable analysis results.

Heart rate variability (HRV) analysis is one example of noninvasive measuring technology. HRV analysis is a method of analyzing the physiological function of the heart on the basis of the heartbeat period sequence. The standard analyzing procedure was defined in the Task Force of the European Society of Cardiology and the North American Society of Pacing and Electrophysiology in 1996. HRV analysis allows measurement of the electrocardiogram signal by electrodes on the body surface, and may obtain a quantitative index of the autonomic nervous system function after complex digital signal processing.

The research team of the present invention uses HRV analysis technology to successfully diagnose body system functions or diseases, such as deep anesthesia, brain death, serious disease prognosis, aging and gender difference.

The noninvasive measuring technology mainly includes two parts: one is the sensor, and the other is the digital signal processing. The development of the sensor is the source of the technology; if no appropriate sensor could be used, the exact digital signal processing would be useless. However, even if a suitable sensor exists, the objective of making the subject relaxed and comfortable with the noninvasive measuring technology still cannot be fully achieved if the manner of use is not convenient. Therefore, it is critical for the development of the noninvasive measuring technology to invent a sensor with functional, comfortable and convenient characteristics.

BRIEF SUMMARY OF THE INVENTION

The present invention provides an earphone sensor system for measuring electrocardiogram signals, which provides convenient and comfortable noninvasive electrocardiogram signal measuring for the subject, so as to obtain HRV related physiological data such as heart function and autonomic nervous system function.

The electrocardiogram signal measuring system comprises an electrocardiogram signal analyzing apparatus and an earphone sensing apparatus. The subject wears the earphone sensing apparatus on the head, wears the electrocardiogram signal analyzing apparatus on the wrist or holds the electrocardiogram signal analyzing apparatus in hand, so as to measure the electrocardiogram signal.

The electrocardiogram signal analyzing apparatus comprises an amplifier module, a microcontroller and a housing having conductive contacts. The earphone sensing apparatus comprises an earphone and an electrode. The electrode is disposed inside the earphone, and can be electrically connected to the subject for collecting weak electrocardiogram signals on the subject's head. As the subject's body surface is in contact with the housing having conductive contacts and the electrode, a basic loop for collecting the electrocardiogram signals is formed. The housing having conductive contacts is considered a ground electrode.

The amplifier module amplifies the electrocardiogram signal, and generates an amplified electrocardiogram signal. The microcontroller performs analog-to-digital conversion on the amplified electrocardiogram signal, so as to generate a digital electrocardiogram signal, and performs the Fourier Transform and digital signal processing of spectrum analysis on the digital electrocardiogram signal, so as to calculate the HRV related physiological data.

The electrocardiogram signal analyzing apparatus may further comprise a display for displaying the digital electrocardiogram signal on the screen of the display for monitoring.

The electrocardiogram signal analyzing apparatus may further comprise a radio module for modulating the digital electrocardiogram signal, transmitting the modulated digital electrocardiogram signal to a remote monitor in a wireless transmission manner, and receiving a wireless signal from the remote monitor.

Because the electrode used to sense the electrocardiogram signal is integrated as one piece with the earphone, it is suitable to be applied to personal electronic products such as Walkmans, mobile phones or watches.

In addition to the electrocardiogram signal, the electrocardiogram signal measuring system can also measure other physiological signals, such as brain waves and body temperature. If the collection of the physiological signals is assisted by the appropriate hardware and software, the medical function can be enhanced. The user may even listen to music while measuring the electrocardiogram, so it is very convenient and the measuring manner will not be seen as strange by others. Moreover, if the health care function is combined with music, it may also be applied in music treatment and bio-feedback.

Other advantages of the present invention are as follows:
(1) The earphone sensing apparatus does not use patch type electrodes; it is not necessary to adhere or take off the electrodes when using them, thus avoiding many inconveniences, and eliminating the cost of patches.
(2) The subject only needs to wear the earphone sensing apparatus on the head, wearing the electrocardiogram signal analyzing apparatus on the wrist or holding the electrocardiogram signal analyzing apparatus in hand, so that the electrocardiogram signal can be measured. It is quite convenient to be used by healthy people, patients or even patients in the intensive care unit.
(3) The electrocardiogram signal analyzing apparatus can transmit the digital electrocardiogram signal to a remote monitor in a wireless transmission manner, thus being convenient for remotely monitoring the electrocardiogram signal of the patient.

DETAILED DESCRIPTION OF THE INVENTION

Figure 1A:
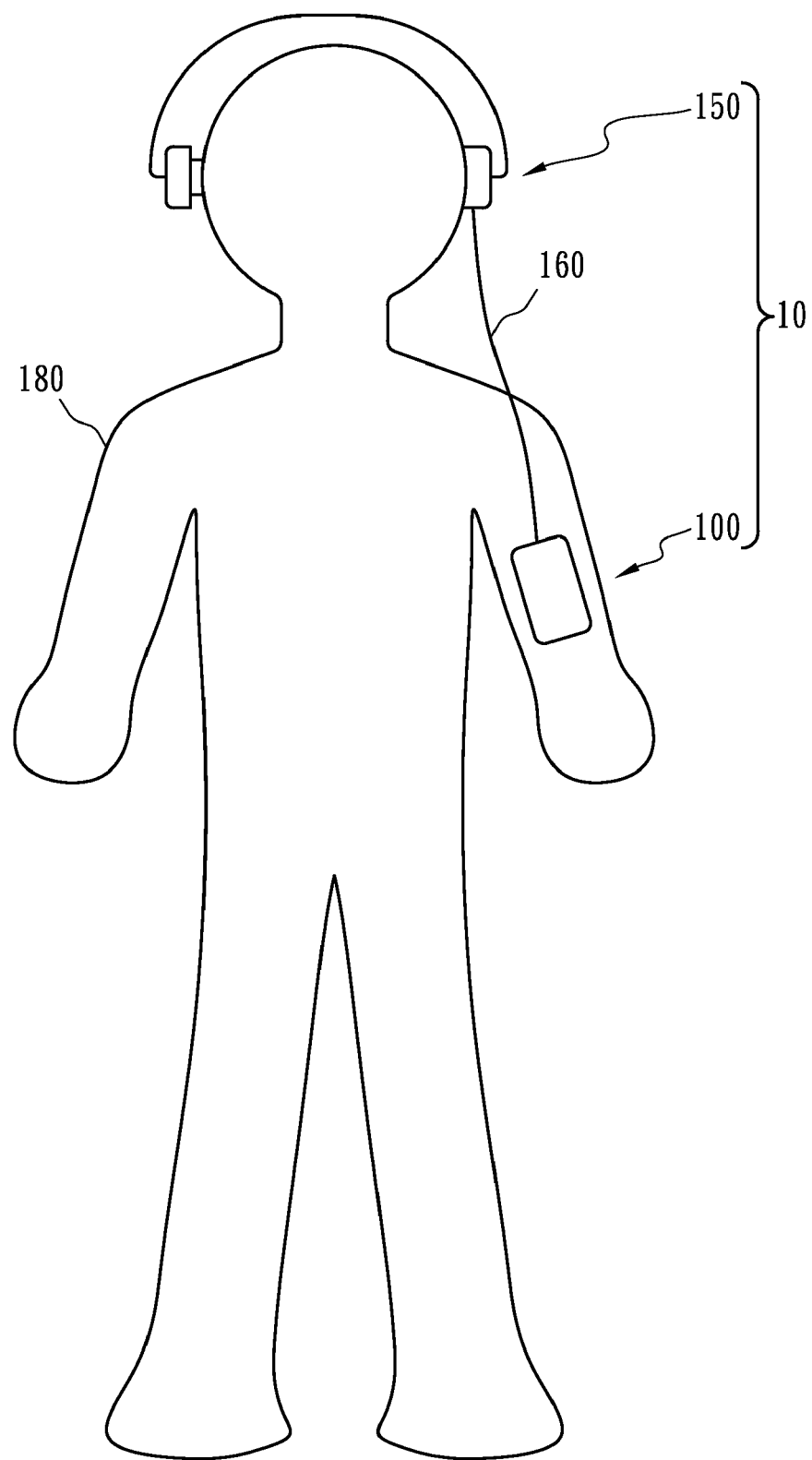
FIG. 1(a) is a schematic view of the application of the earphone sensor system for measuring electrocardiogram signals according to an embodiment of the present invention.

FIG. 1(a) is a schematic view of the application of the earphone sensor system 10 for measuring electrocardiogram signals according to an embodiment of the present invention. The electrocardiogram signal measuring system 10 includes an electrocardiogram signal analyzing apparatus 100 and an earphone sensing apparatus 150, with the two electrically connected through a signal line 160. A subject 180 wears the earphone sensing apparatus 150 on the head, wears the electrocardiogram signal analyzing apparatus 100 on the wrist or holds the electrocardiogram signal analyzing apparatus 100 in hand, so as to perform the electrocardiogram signal measuring.

Figure 1B:
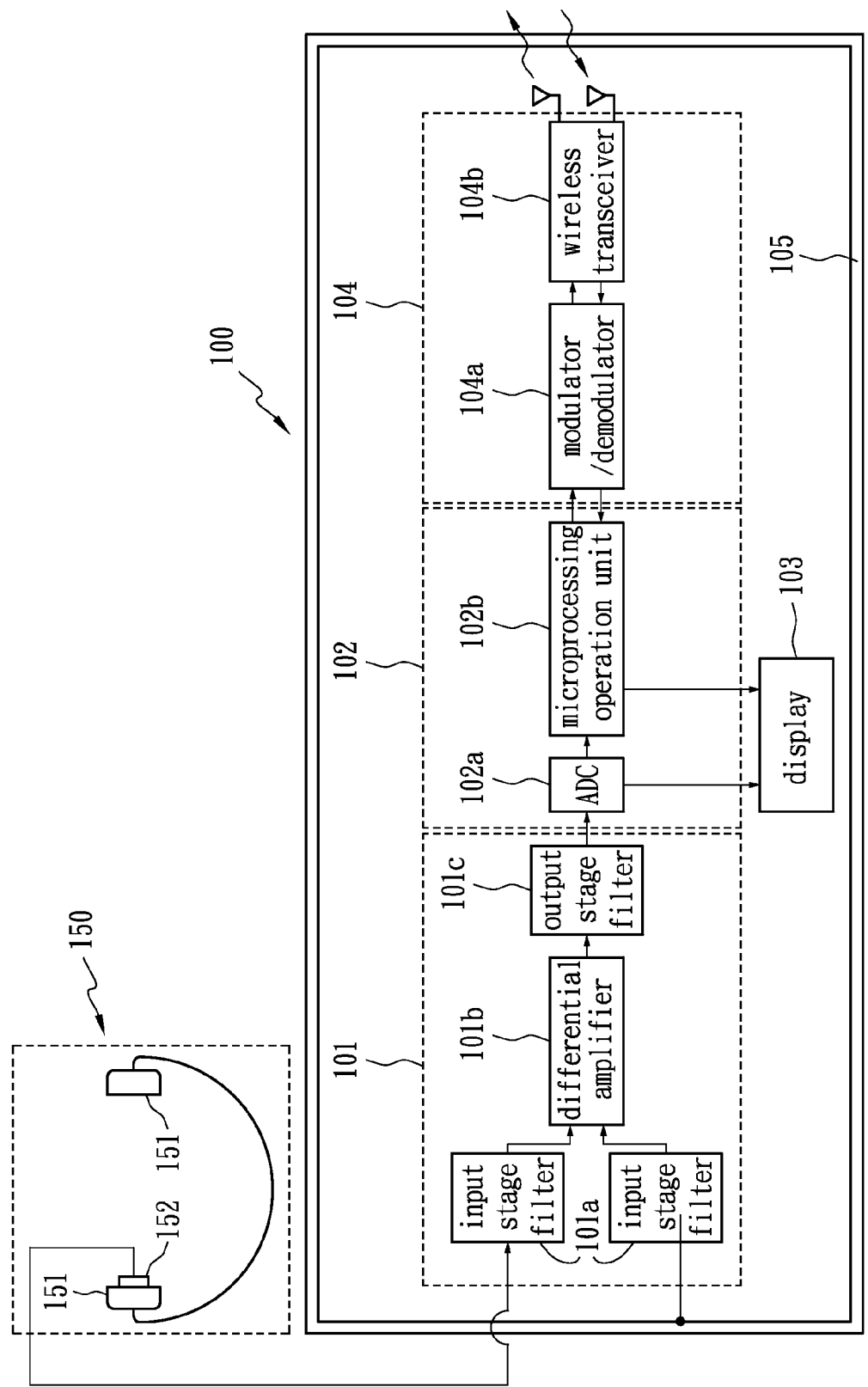
FIG. 1(b) is a schematic view of a block diagram of the electrocardiogram signal analyzing apparatus and the earphone sensing apparatus according to an embodiment of the present invention.

As shown in FIG. 1(b), the earphone sensing apparatus 150 includes an earphone 151 and an electrode 152, and the earphone 151 can be of single-ear type or double-ear type. The electrocardiogram signal analyzing apparatus 100 includes an amplifier module 101, a microcontroller 102, a display 103, a radio module 104 and a housing having conductive contacts 105.

The electrode 152 is disposed inside the earphone 151 and collects the weak electrocardiogram signal of the head of the subject 180. Because the body surface of the testee 180 is in contact with the housing having conductive contacts 105 and the electrode 152, a basic loop for collecting the electrocardiogram signal is formed, and the housing having conductive contacts 105 is considered as a ground electrode.

The amplifier module 101 includes a pair of input stage filters 101a, a differential amplifier 101b and an output stage filter 101c. The pair of input stage filters 101a respectively receive the input signals from the electrode 152 and the housing having conductive contacts 105, and then filter the noise to increase the signal to noise ratio. A differential amplifying is performed on the signals by the differential amplifier 101b, so as to generate an amplified electrocardiogram signal. The differential amplifier 101b attenuates the common mode noise, and, meanwhile, amplifies the differential electrocardiogram signal by an appropriate magnification, so as to be in accordance with the voltage range of the analog-to-digital conversion of the microcontroller 102. The output stage filter 101c filters the signal with the frequency higher than the Nyquist frequency (i.e. twice the sampling frequency in the analog-to-digital conversion of the microcontroller) from the amplified electrocardiogram signal, so as to facilitate the analog-digital sampling of the microcontroller 102. Moreover, the impedance of the input end of the amplifier module 101 is larger than 200 kΩ, so as to avoid the current leakage caused by wrong actions. The input stage filters 101a and the output stage filter 101c may be formed by the resistive or capacitive passive elements, and the differential amplifier 101b may be formed by an integrated circuit operational amplifier or an instrumentation amplifier.

The microcontroller 102 includes an analog-to-digital conversion unit 102a and a microprocessing operation unit 102b configured to perform digital signal processing on the amplified electrocardiogram signal. The analog-to-digital conversion unit 102a performs the analog-to-digital conversion on the amplified electrocardiogram signal generated by the amplifier module 101 with appropriate voltage resolution and sampling rate, so as to generate a digital electrocardiogram signal. Then, the microprocessing operation unit 102b performs the Fourier Transform and the digital signal processing of spectrum analysis on the digital electrocardiogram signal, so as to calculate the HRV related physiological data.

The display 103 displays the digital electrocardiogram signal or HRV related physiological data on the screen of the display 103 for monitoring.

The radio module 104 includes a wireless transceiver 104b and a modulator/demodulator 104a. The radio module 104 receives the digital electrocardiogram signal generated by the microcontroller 102, and the digital electrocardiogram signal is modulated by the modulator/demodulator 104a to a modulated electrocardiogram signal with the carrier of 2.4 GHz. The modulated electrocardiogram signal is sent to a remote monitor as a wireless electrocardiogram signal by the wireless transceiver 104b. Meanwhile, the wireless transceiver 104b can also receive the wireless signal from the remote monitor. The wireless signal is demodulated by the modulator/demodulator 104a to the digital data signal, and is sent to the microcontroller 102. The radio module 104 performs radio transmission and receiving in a 2.4 GHz Industry Science Medical (ISM) frequency band according to International Standards.

Figure 2:
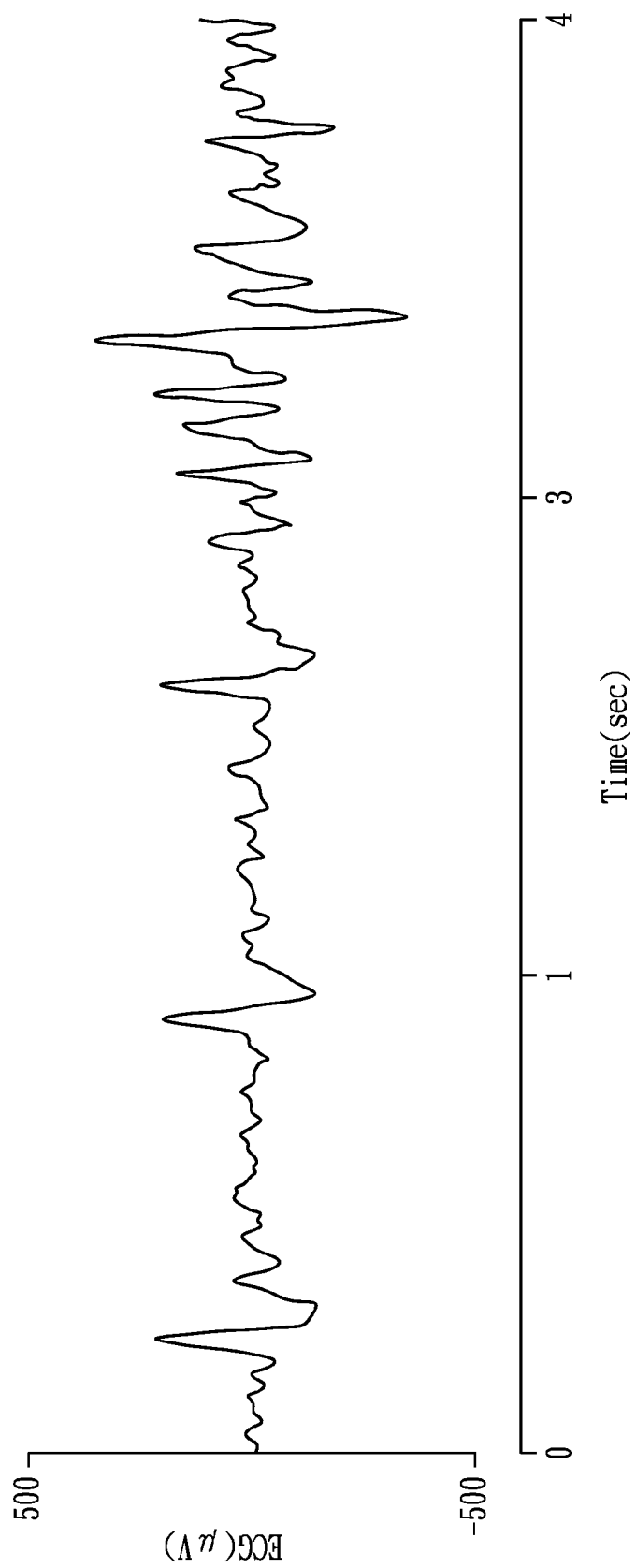
FIG. 2 is an oscillogram of the electrocardiogram signals collected by the earphone sensor system for measuring electrocardiogram signals according to the present invention.

FIG. 2 is the wave pattern of the electrocardiogram signals collected by the earphone sensor system 10 for measuring electrocardiogram signals of the present invention displayed on the display 103.

The above-described embodiments of the present invention are intended to be illustrative only. Numerous alternative embodiments may be devised by those skilled in the art without departing from the scope of the following claims.

We claim:
1. An earphone sensor system for measuring electrocardiogram signals comprising:
   an earphone;
   an electrode disposed in the earphone suitable for being electrically connected to the head of the subject so as to collect an analog electrocardiogram signal from a head of a subject, said earphone and said electrode being integrally formed together; and an electrocardiogram signal analyzer electrically connected to said earphone, said electrocardiogram signal analyzer suitable for performing a digital signal processing on the electrocardiogram signal so as to generate a digital electrocardiogram signal, said electrocardiogram analyzer comprising a display suitable for displaying the digital electrocardiogram signal on a screen of said display.

2. The earphone sensor system of claim 1, wherein the electrocardiogram signal analyzer comprises:
an amplifier module suitable for amplifying the electrocardiogram signal to generate an amplified electrocardiogram signal;
a microcontroller suitable for performing digital signal processing on the amplified electrocardiogram signal; and
a housing having conductive contacts suitable for serving as a ground electrode, said housing and said electrode forming a collecting loop when connected to the head of the subject.

3. The earphone sensor system of claim 2, wherein the electrocardiogram signal analyzer apparatus further comprises a radio module suitable for modulating the digital electrocardiogram signal and transmitting the modulated digital electrocardiogram signal to a remote monitor in a wireless transmission manner.

4. The earphone sensor system of claim 2, wherein the radio module is for receiving a wireless signal from the remote monitor.

5. The earphone sensor system of claim 2, wherein the amplifier module comprises a pair of input stage filters respectively electrically connected to the electrode and the housing, said pair of input stage filters suitable for filtering noise.

6. The earphone sensor system of claim 2, wherein the amplifier module comprises a differential amplifier for differentially amplifying the electrocardiogram signal to generate the amplified electrocardiogram signal so as to conform with a voltage range of an analog-to-digital conversion of the microcontroller.

7. The earphone sensor system of claim 6, wherein the differential amplifier is formed by an integrated circuit operational amplifier.

8. The earphone sensor of claim 6, wherein the differential amplifier is formed by an instrumentation amplifier.

9. The earphone sensor system of claim 2, wherein the amplifier module comprises an output stage filter suitable for filtering the signal having a frequency higher than twice a sampling frequency in an analog-to-digital conversion by the microcontroller.

10. The earphone sensor system of claim 2, wherein an impedance of an input end of said amplifier module is larger than 200 kΩ.

11. The earphone sensor system of claim 2, wherein said microcontroller comprises:
an analog-to-digital conversion unit connected to the amplifier module, said analog-to-digital conversion unit suitable for performing analog-to-digital conversion on the amplified electrocardiogram signal with a voltage resolution and a sampling rate so as to generate the digital electrocardiogram signal; and
a microprocessing operation unit connected to said analog-to-digital conversion unit, said microprocessor operation unit suitable for performing a Fourier Transform and a digital signal processing of a spectrum analysis on the digital electrocardiogram signal, so as to calculate a heart rate variability (HRV) data.

12. The earphone sensor system of claim 3, wherein said radio module comprises:
a modulator/demodulator for suitable modulating the digital electrocardiogram signal into a modulated electrocardiogram signal; and
a wireless transceiver suitable for sending the modulated electrocardiogram signal to said remote monitor in a wireless transmission manner.

13. The earphone sensor system of claim 3, wherein said radio module is suitable for performing radio transmission and receiving in a 2.4 GHz Industry Science Medical (ISM) frequency band.

14. The earphone sensor system of claim 1, wherein said earphone is a single-ear earphone.

15. The earphone sensor system of claim 1, wherein said earphone is a double-ear-phone.

* * * * *